US008606809B2

(12) United States Patent
Kato et al.

(10) Patent No.: US 8,606,809 B2
(45) Date of Patent: Dec. 10, 2013

(54) PROGRAM RECORDING MEDIUM, COMPUTER, AND CULTURE STATE ANALYZING METHOD

(75) Inventors: Hidemasa Kato, Iruma-gun (JP); Yasujiro Kiyota, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/662,401

(22) Filed: Apr. 15, 2010

(65) Prior Publication Data

US 2010/0274798 A1 Oct. 28, 2010

Related U.S. Application Data

(63) Continuation of application No. PCT/JP2008/002920, filed on Oct. 15, 2008.

(30) Foreign Application Priority Data

Oct. 19, 2007 (JP) .................................. 2007-272755

(51) Int. Cl.
*G06F 17/30* (2006.01)

(52) U.S. Cl.
USPC ........................................................ 707/769

(58) Field of Classification Search
USPC ........................................................ 707/769
See application file for complete search history.

(56) References Cited

U.S. PATENT DOCUMENTS

| | | | | |
|---|---|---|---|---|
| 6,631,331 | B1 * | 10/2003 | Sabry et al. ...................... | 702/19 |
| 6,738,716 | B1 * | 5/2004 | Sabry et al. ...................... | 702/19 |
| 6,804,679 | B2 * | 10/2004 | Jevons et al. ........................ | 1/1 |
| 6,816,867 | B2 * | 11/2004 | Jevons et al. ........................ | 1/1 |
| 6,834,122 | B2 * | 12/2004 | Yang et al. ..................... | 382/227 |
| 7,065,451 | B2 * | 6/2006 | Garner et al. ................... | 702/20 |
| 7,565,247 | B1 * | 7/2009 | Dunlay et al. .................. | 702/19 |
| 2005/0282268 | A1 | 12/2005 | Kagayama | |

FOREIGN PATENT DOCUMENTS

| | | |
|---|---|---|
| JP | 2004-54347 | 2/2004 |
| JP | 2006-11415 | 1/2006 |
| JP | 2006-017489 | 1/2006 |
| JP | 2006-018394 | 1/2006 |
| JP | 2006-055027 | 3/2006 |
| JP | 2007-006852 | 1/2007 |
| JP | 2007-011977 | 1/2007 |
| JP | 2007-020422 | 2/2007 |
| JP | 2007-108154 | 4/2007 |

OTHER PUBLICATIONS

International Search Report, Form PTO/ISA/210, dated Dec. 16, 2008.
International Preliminary Report on Patentability, Form PCT/IB/326, Dated Apr. 29, 2010.
International Preliminary Report on Patentability, Form PCT/IB/338/373, Dated May 20, 2010.
Japanese Office Action issued Sep. 3, 2013 in corresponding Japanese Application No. 2009-537919.

* cited by examiner

*Primary Examiner* — Sheree Brown

(57) ABSTRACT

In one aspect of an embodiment, a computer determines an identity of the cells with a cell shape data, and also determines a correspondence relationship of identification data between a plurality of cell analyzing tables at a different observing times. Also, the computer, based on the correspondence relationship of the identification data, records a plurality of cell analyzing tables at the different observing times in a storage medium by making into a database which can be searched in a direction of a time axis for each of the cells having commonality.

10 Claims, 11 Drawing Sheets

FIG.10

PROGRAM RECORDING MEDIUM, COMPUTER, AND CULTURE STATE ANALYZING METHOD

CROSS REFERENCE TO RELATED APPLICATION

This application is a continuation application of International Application PCT/JP2008/002920, filed Oct. 15, 2008, designating the U.S., and claims the benefit of priority from Japanese Patent Application No. 2007-272755, filed on Oct. 19, 2007, the entire contents of which are incorporated herein by reference.

BACKGROUND

1. Field

The present application relates to a program recording medium, a computer, and a culture state analyzing method.

2. Description of the Related Art

Conventionally, there are known culture devices that culture cells in a temperature-controlled room maintained in a predetermined atmosphere. In order to evaluate the state of the cells cultured in the culture device, it is proposed to combine a transparent observing image (bright field observation image) and a fluorescence image of the cells obtained by imaging an identical field and to analyze the shape and the fluorescence expression states of the cells at a specific observing time point. In Japanese Unexamined Patent Application Publication No. 2004-54347, there is disclosed a technology that uses a phase-contrast image and a fluorescence image to extract the outline of a cell.

BRIEF DESCRIPTION OF THE DRAWINGS

FIG. 10 is a diagram showing an example of a display screen listing cell shape data and the like at each observing time point.

DETAILED DESCRIPTION OF THE EMBODIMENT

Description of the Configuration of a Culture Device

Figure 1:
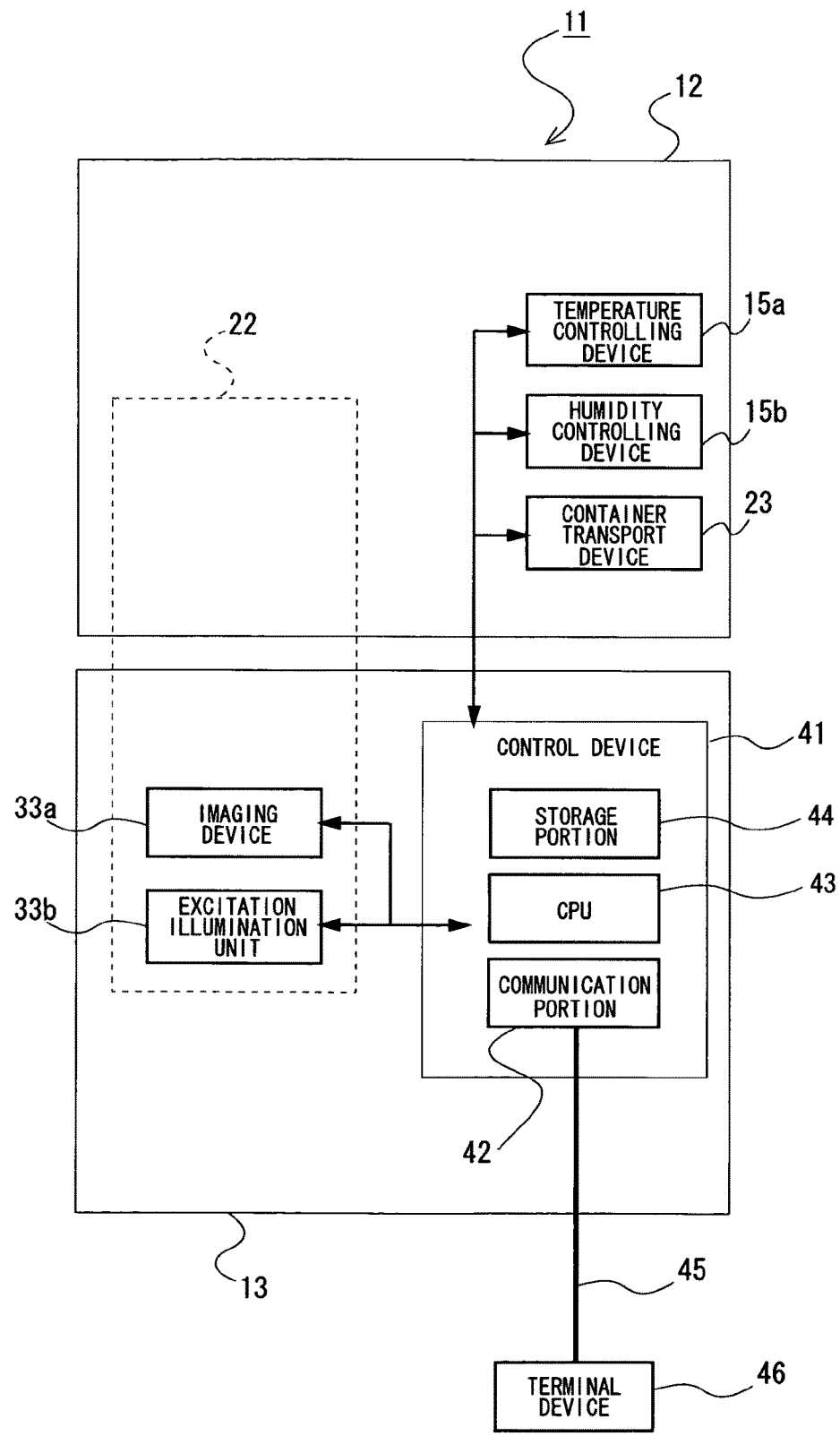
FIG. 1 is a block diagram of a culture device of the present embodiment.
Figure 2:
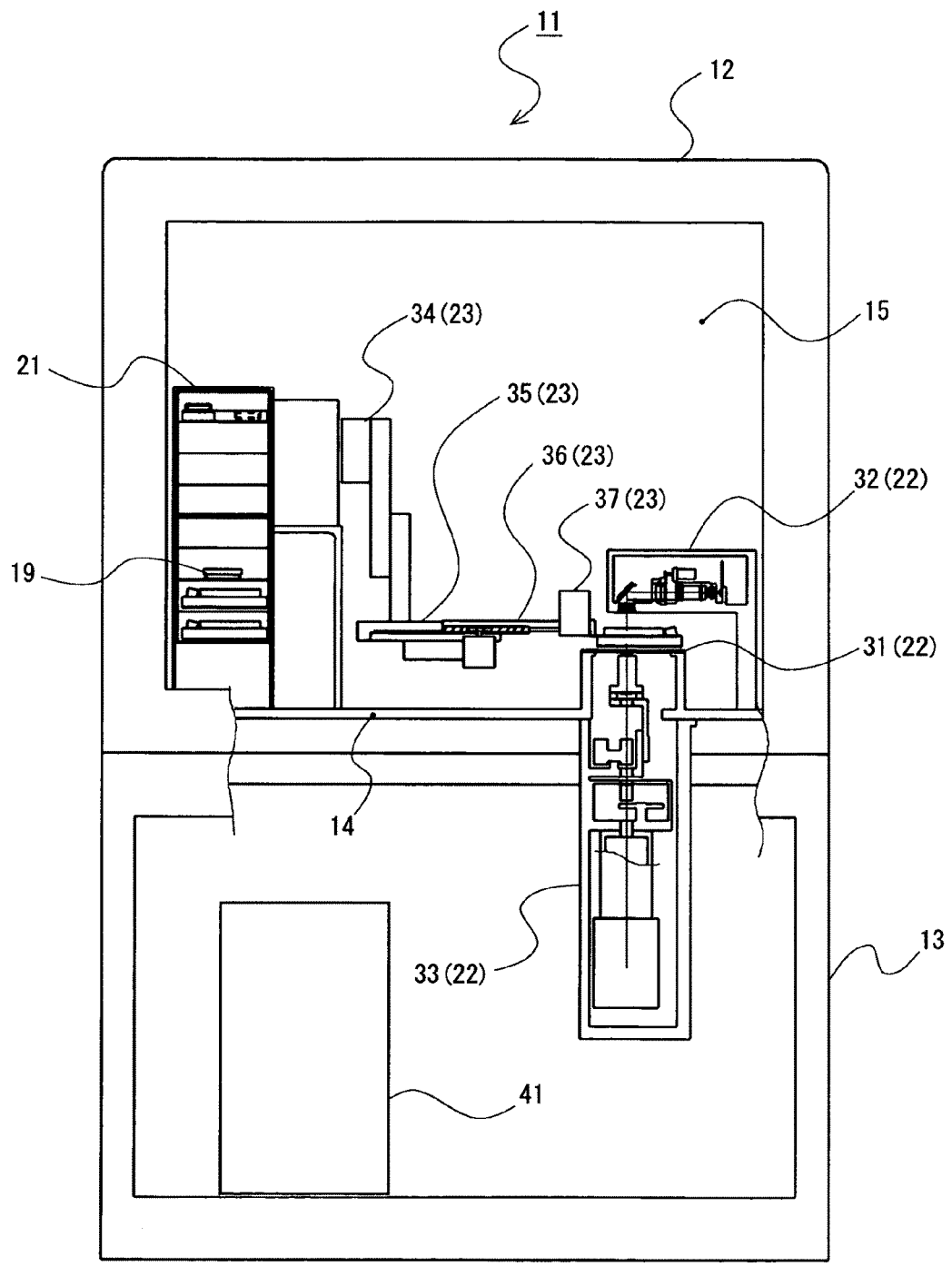
FIG. 2 is a front view of the culture device of the present embodiment.
Figure 3:
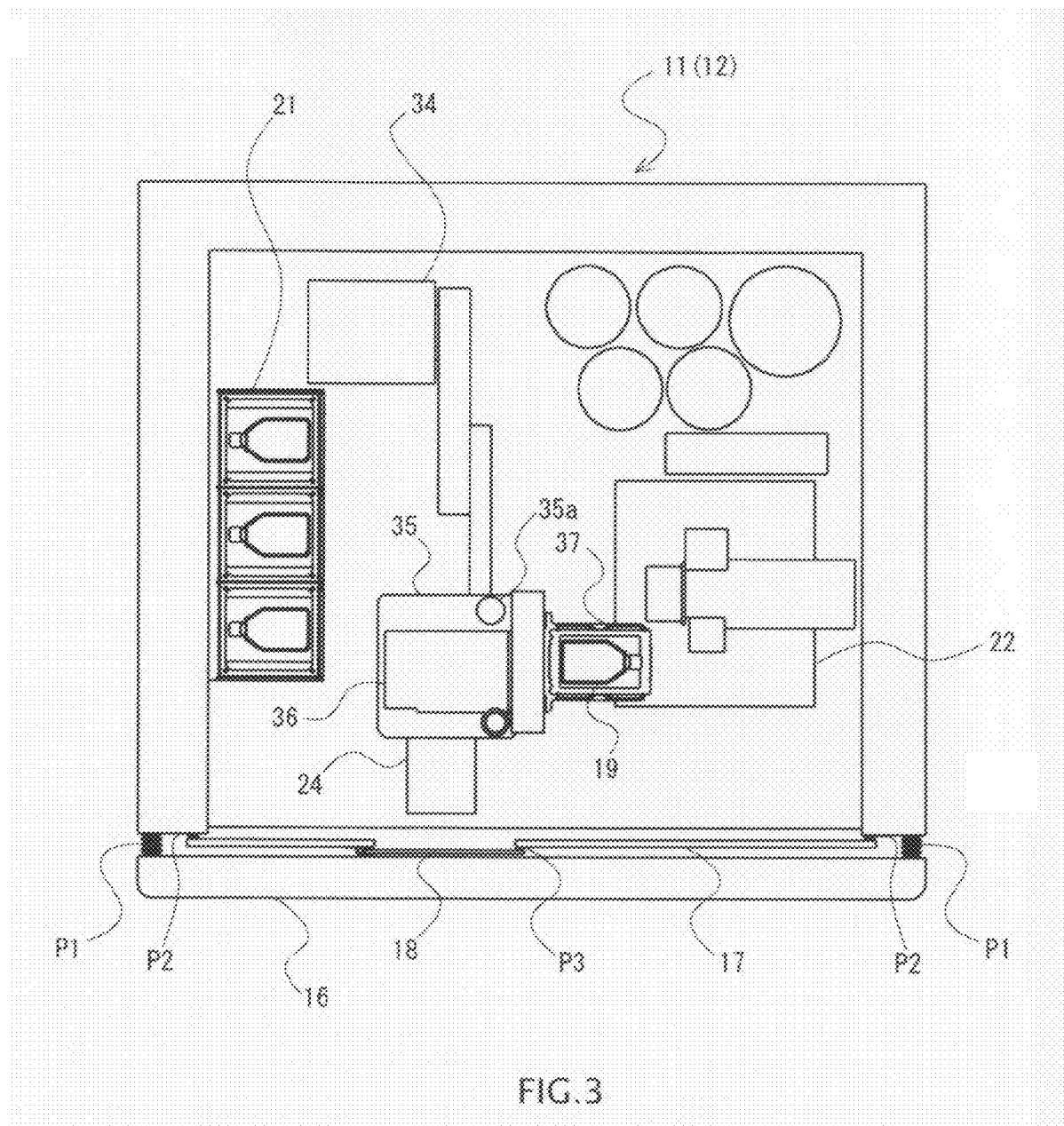
FIG. 3 is a plan view of the culture device of the present embodiment.

The configuration of a culture device of the present embodiment will be described below with reference to the accompanying drawings. FIG. 1 is a block diagram of the culture device of the present embodiment. FIGS. 2 and 3 are front view and plan view of the culture device of the present embodiment.

A culture device 11 of the present embodiment includes an upper casing 12 and a lower casing 13. In the assembled state of the culture device 11, the upper casing 12 is placed on the lower casing 13. The inner space of the upper casing 12 and the lower casing 13 is divided by a base plate 14 into an upper space and a lower space.

The configuration of the upper casing 12 will first be schematically described. Within the upper casing 12, a temperature-controlled room 15 for culturing cells is formed. This temperature-controlled room 15 includes a temperature controlling device 15a and a humidity controlling device 15b, the temperature-controlled room 15 is maintained in an environment (for example, at a temperature of 37° C. and a humidity of 90%) suitable for culturing cells (in FIGS. 2 and 3, the temperature controlling device 15a and the humidity controlling device 15b are not shown.)

On the front surface of the temperature-controlled room 15, a large-sized door 16, a medium-sized door 17, and a small-sized door 18 are arranged. The large-sized door 16 covers the front surface of the upper casing 12 and the lower casing 13. The medium-sized door 17 covers the front surface of the upper casing 12, when the large-sized door 16 is opened, the medium-sized door 17 separates the temperature-controlled room 15 from the outside environment. The small-sized door 18 is a door through which a culture container 19 for culturing cells is inserted and removed, the small-sized door 18 is attached to the medium-sized door 17. The insertion and removal of the culture container 19 through the small-sized door 18 can reduce variations in the environment of the temperature-controlled room 15. The hermeticity of the large-sized door 16, the medium-sized door 17, and the small-sized door 18 is maintained with packing units P1, P2, and P3, respectively.

In the temperature-controlled room 15, a stocker 21, an observation unit 22, a container transport device 23, and a transport stage 24 are arranged. Here, the transport stage 24 is arranged in front of the small-sized door 18, and inserts and removes the culture container 19 through the small-sized door 18.

The stocker 21 is arranged on the left side of the temperature-controlled room 15 as seen from the front surface (the lower side of FIG. 3) of the upper casing 12. The stocker 21 has a plurality of shelves; a plurality of culture containers 19 can be stored in each shelf of the stocker 21. Cells along with a culture medium are stored in each of the culture containers 19.

The observation unit 22 is arranged on the right side of the temperature-controlled room 15 as seen from the front surface of the upper casing 12. This observation unit 22 allows time lapse observation to be performed on the cells within the culture container 19.

This observation unit 22 is arranged to be fitted into an opening in the base plate 14 of the upper casing 12. The observation unit 22 is provided with a specimen stage 31, a stand arm 32 that protrudes upward from the specimen stage 31, and a main body portion 33 that incorporates a microscopic optical system and an imaging device (33a). The specimen stage 31 and the stand arm 32 are arranged in the temperature-controlled room 15, and the main body portion 33 is housed within the lower casing 13.

The specimen stage 31 is formed of a translucent material, and the culture container 19 can be placed thereon. This specimen stage 31 is configured such that it can move horizontally, and thus it is possible to adjust the position of the culture container 19 placed on the upper surface. Moreover, the stand arm 32 incorporates an LED light source. The imaging device 33a images the cells in the culture container 19 that are illuminated by the stand arm 32 from above the specimen stage 31 therethrough, and thereby can acquire a phase-contrast image.

The main body portion 33 of the observation unit 22 is provided with an excitation illumination unit (33b) for fluorescence observation. The imaging device 33a images, through the microscopic optical system, fluorescence that is expressed from the cells by the epi-illumination of the excitation light, and thus can acquire the fluorescence image of the cells.

The container transport device 23 is arranged in the middle of the temperature-controlled room 15 as seen from the front surface of the upper casing 12. This container transport device 23 transports the culture container 19 between the stocker 21, the specimen stage 31 of the observation unit 22, and the transport stage 24.

As shown in FIG. 3, the container transport device 23 is provided with a vertical robot 34 having a multi-jointed arm, a rotary stage 35, a mini-stage 36, and an arm portion 37. The rotary stage 35 is attached through a rotary shaft 35a to the end portion of the vertical robot 34 such that the rotary stage 35 can turn 180 degrees in the horizontal direction. Hence, the rotary stage 35 allows the arm portion 37 to face the stocker 21, the specimen stage 31, and the transport stage 24.

The mini-stage 36 is attached such that it can slide with respect to the rotary stage 35 in the horizontal direction. The arm portion 37 for holding the culture container 19 is attached to the mini-stage 36.

The configuration of the lower casing 13 will now be schematically described. Within the lower casing 13, the main body portion 33 of the observation unit 22, and a control device 41 for collectively controlling the individual portions of the culture device 11 are housed.

The control device 41 is connected to the temperature controlling device 15a, the humidity controlling device 15b, the observation unit 22, and the container transport device 23. This control device 41 collectively controls the individual portions of the culture device 11 according to a predetermined program. For example, the control device 41 individually controls the temperature controlling device 15a and the humidity controlling device 15b to maintain predetermined environment conditions within the temperature-controlled room 15. The control device 41 controls the observation unit 22 and the container transport device 23 based on a predetermined observation schedule to automatically perform an observation sequence of the culture container 19.

The control device 41 is provided with a communication portion 42, a CPU 43, and a storage portion 44. The communication portion 42 and the storage portion 44 are connected to the CPU 43.

The communication portion 42 exchanges, through a wireless or wired communication line 45, data with a terminal device 46 that is provided outside the culture device 11. As this terminal device 46, for example, a common personal computer can be used. The terminal device 46 includes an output device such as a monitor or a printer and an input device such as a keyboard or a pointing device (they are not shown.)

The CPU 43 is a processor that performs various computations on the control device 41. The CPU 43 performs a program to analyze the phase-contrast image and the fluorescence image acquired from the imaging device 33a, and generates a cell analyzing table from the result of the analysis (the cell analyzing table will be described later).

The storage portion 44 is formed with a nonvolatile storage medium such as a hard disk or a flash memory. This storage portion 44 stores control data on the culture containers 19 stored in the stocker 21, data on the phase-contrast image and the fluorescence image and data on the cell analyzing table.

The control data includes the following (a) index data indicating the individual culture containers 19, (b) the positions at which the culture containers 19 are stored in the stocker 21, (c) the type and shape of the culture containers 19 (such as a well plate, a dish and a flask), (d) the type of cells cultured in the culture containers 19, (e) information on medical agents put into the culture containers 19, (f) the observation schedule on the culture containers 19, and (g) imaging conditions at the time of the time lapse observation (such as the magnification of an objective lens and the observation point within the container). For the culture container 19 that can simultaneously culture cells in a plurality of small containers as with the well plate, the control data is generated for each of the small containers.

(Description of an Observation Operation within the Culture Device)

An example of an observation operation in the culture device 11 of the present embodiment will be described below with reference to the flowchart of FIG. 4. Here, as the example below, a case where the time lapse observation is performed, according to a registered observation schedule, on the culture container 19 transported in the temperature-controlled room 15 will be described.

Here, in the example below, a case where cells into which a gene of a fluorescence protein such as a GFP (green fluorescent protein) is introduced are observed will be described. In order for a proper resolution in the direction of a time axis to be acquired when the analysis of the cell cycle is performed, the interval of the time lapse observation is set at least shorter than the division cycle of the cells to be observed. Preferably, the interval of the time lapse observation is set shorter than the duration of the constant condition to be observed in the cell cycle.

In step S101, the CPU 43 compares the observation schedule of the control data stored in the storage portion 44 with the current time to determine whether or not the observation start time of the culture container 19 is reached. If the observation start time is reached (yes), the process proceeds to step S102. On the other hand, if the observing time of the culture container 19 is not reached (no), the CPU 43 is placed on standby until the next time of the observation schedule is reached.

In step S102, the CPU 43 instructs the container transport device 23 to transport the culture container 19 according to the observation schedule. Then, the container transport device 23 transports the indicated culture container 19 from the stocker 21, and places it on the specimen stage 31 of the observation unit 22. When the culture container 19 is placed on the specimen stage 31, a bird's eye view camera (not shown) incorporated in the stand arm 32 captures the entire observation image of the culture container 19.

In step S103, the CPU 43 instructs the observation unit 22 to capture the phase-contrast image of the cells. The observation unit 22 turns on the light source of the stand arm 32 to illuminate the culture container 19. Then, the imaging device 33a of the observation unit 22 captures the phase-contrast image of the cells within the culture container 19. Here, the imaging device 33a captures the phase-contrast image based both on the control data stored in the storage portion 44 and the imaging conditions (the magnification of the objective lens and the observation point within the container) specified by a user. The data of the phase-contrast image is input to the control device 41, and is recorded in the storage portion 44 by the CPU 43.

In step S104, immediately after the phase-contrast image is captured (S103), the CPU 43 instructs the observation unit 22 to capture the fluorescence image of the cells. The observation unit 22 directs the excitation light from the excitation illumination unit 33b onto the cells from above, and the imaging device 33a captures the fluorescence image of the cells within the culture container 19. The scope of the field captured in step S104 by the imaging device 33a is set equal to the scope of the field for the phase-contrast image. The data of the fluorescence image is input to the control device 41, and is recorded in the storage portion 44 by the CPU 43.

Figure 4:
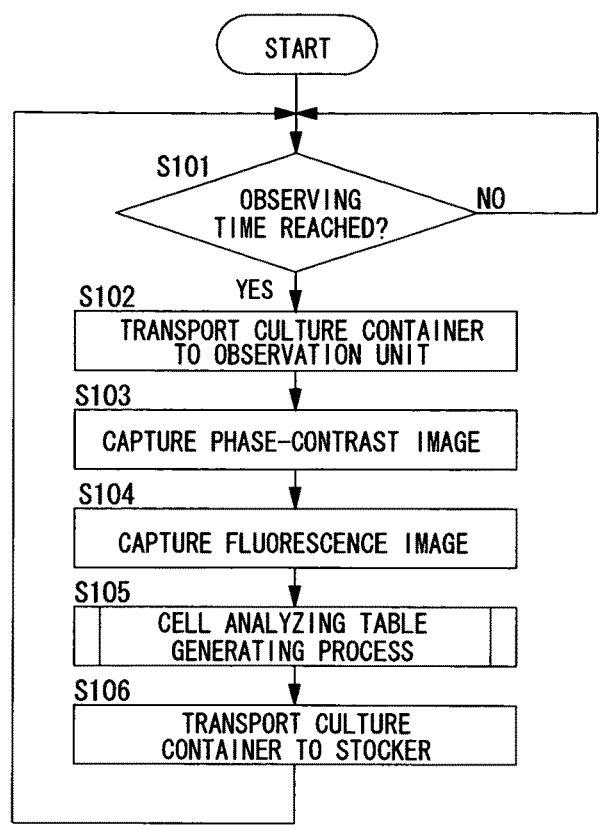
FIG. 4 is a flowchart showing an example of an observation operation performed in the culture device of the present embodiment.

Here, when a plurality of points within the culture container 19 is observed, for each of the points, the observation unit 22 repeats the operations in steps S103 and S104 to generate a set of the phase-contrast image and the fluorescence image of an identical field (the loop in this case is not shown in FIG. 4.)

In step S105, the CPU 43 analyzes the data of the phase-contrast image (S103) and the data of the fluorescence image (S104) to generate the cell analyzing table.

In step S106, after the completion of the observation schedule, the CPU 43 instructs the container transport device 23 to transport the culture container 19. Then, the container transport device 23 transports the indicated culture container 19 from the specimen stage 31 of the observation unit 22 to a predetermined storage position of the stocker 21, and then the observation sequence is completed and the process returns to step S101. Here, the description of the flowchart of FIG. 4 is completed.

(Description of the Cell Analyzing Table Generating Process)

Figure 5:
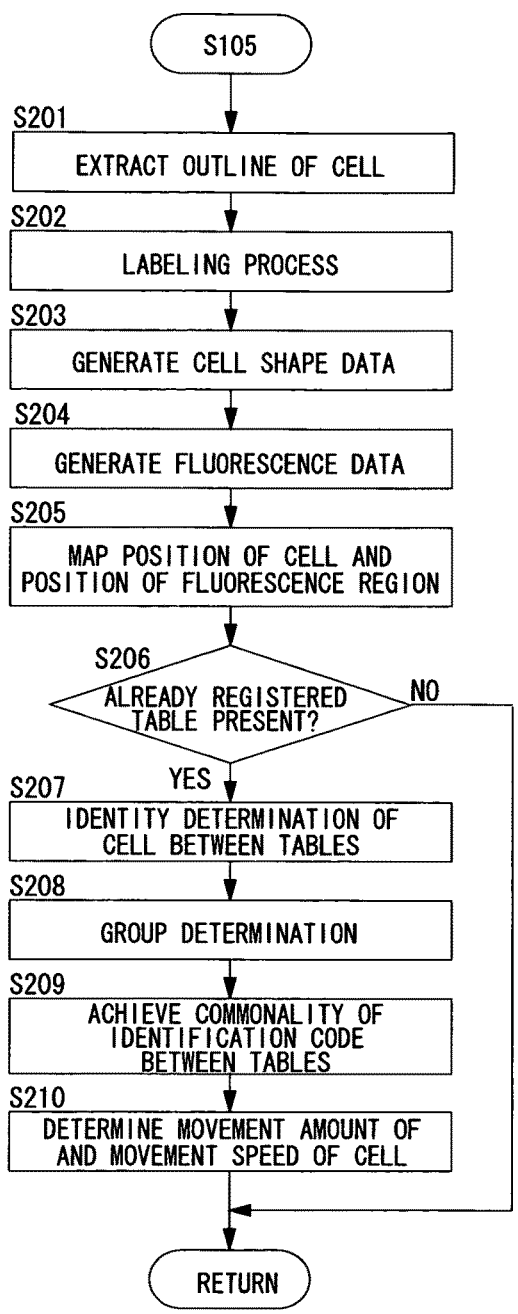
FIG. 5 is a flowchart showing the subroutine of a cell analyzing table generating process performed in S105 of FIG. 4.

FIG. 5 is a flowchart showing the subroutine of the cell analyzing table generating process performed in S105 of FIG. 4.

In step S201, the CPU 43 reads the data of the phase-contrast image (S103) from the storage portion 44, and extracts the individual cells included in the phase-contrast image.

For example, when the cells are imaged by a phase-contrast microscope, halos appear around portions, such as a cell wall or cell membrane, in which the phase difference is varied significantly. Hence, the CPU 43 extracts a halo corresponding to a cell wall or cell membrane by a known edge extraction method, and estimates a closed space surrounded by the edge as the outline of the cell. In this way, it is possible to extract each cell from the phase-contrast image. In the culture device of the present embodiment, the phase-contrast image and the fluorescence image of the identical field are captured, and thus it is also possible to extract the outline of the cells by using the method described in Japanese Unexamined Patent Application Publication No. 2004-54347 described previously.

In step S202, the CPU 43 performs a labeling process in order to identify the individual cells extracted from the phase-contrast image. Specifically, the CPU 43 gives identification codes (or numbers) to the respective cells extracted from the phase-contrast image.

In step S203, the CPU 43 generates cell shape data indicating the position and the shape of the cell, for each of the cells that have been subjected to the labeling based on the phase-contrast image. Specifically, the CPU 43 performs processes (1) to (6) below.

(1) The CPU 43 determines a target cell for the generation of the cell shape data from the phase-contrast image one by one.

(2) The CPU 43 generates position data of the target cell on the phase-contrast image. The CPU 43 uses a known algorism for the computation of the barycenter to determine the barycenter of the cell of interest, and assumes that the coordinates of the barycenter of the cell of interest on the phase-contrast image are the position data.

(3) The CPU 43 generates the shape data of the cell of interest. The CPU 43 sets a rectangular frame that circumscribes the outline of the cell of interest. Then, the CPU 43 assumes that the ratio (%) of the size of the rectangular frame surrounding the cell of interest to an area occupied by the cell within the rectangular frame is the shape data. The CPU 43 also determines the relative positional relationship between the position of the barycenter of the cell of interest and the rectangular frame.

(4) The CPU 43 records the cell shape data (the position data and the shape data) in the storage portion 44 such that the cell shape data corresponds to the identification code of the cell of interest. The CPU 43 cuts the image within the rectangular frame out of the phase-contrast image, and records the data of this trimming image in the storage portion 44 such that the data corresponds to the identification code of the cell of interest.

(5) The CPU 43 determines, by image analysis, whether the cell of interest is a single cell or an attached cell. For example, the CPU 43 estimates nuclei within the cells based on the outline and the like of the phase-contrast image. Then, the CPU 43 determines, based on the number of nuclei within the outline of the cell walls or cell membranes, whether the cell of interest is a single cell or an attached cell. Alternatively, the CPU 43 may determine, based on the shape and the size of the outline of the cell walls or cell membranes extracted from the phase-contrast image, whether the cell of interest is a single cell or an attached cell.

Then, the CPU 43 generates, based on the results of the determination, attribution data indicating the attribution (a single cell or an attached cell) of the cell of interest. The CPU 43 records this attribution data in the storage portion 44 such that the attribution data corresponds to the identification code of the cell of interest.

(6) The CPU 43 specifies, as a new cell of interest, a cell whose cell shape data and attribution data have not been generated among the cells included in the phase-contrast image. Then, the CPU 43 repeats the processes described in (2) to (5) above to generate the cell shape data and the attribution data for all the cells.

In step S204, the CPU 43 reads the date of the fluorescence image (S104) from the storage portion 44, and generates fluorescence data indicating a fluorescence detection state within the fluorescence image. The CPU 43 first extracts fluorescence regions within the fluorescence image. Then, the CPU 43 determines, for each of the fluorescence regions, the position of the barycenter of the fluorescence region, an area of the fluorescence region and the brightness average value within the fluorescence region, and generates the fluorescence data of each of the fluorescence regions. The CPU 43 stores the fluorescence data in the storage portion 44.

In step S205, the CPU 43 maps the position of each cell extracted from the phase-contrast image and the position of the fluorescence region indicated by the fluorescence data (S204) to determine the relationship between each cell and the fluorescence region. In this way, the CPU 43 specifies which fluorescence region belongs to each of the cells and thus makes the identification code of the cell correspond to the fluorescence data.

Here, when there is a plurality of fluorescence regions within one cell, the CPU 43 makes a plurality of pieces of fluorescence data correspond to one identification code. When there is no fluorescence region within one cell, the CPU 43 makes data indicating there is no fluorescence region within the cell corresponding to an identification code.

The processes in steps S201 to S205 make the cell shape data, the fluorescence data, and the attribution data correspond to each identification code, and the cell analyzing table indicating the state of each cell at a predetermined observing time is generated in the storage portion 44.

In step S206, the CPU 43 determines whether or not a past cell analyzing table on an identical target is stored in the storage portion 44 (that is, whether or not a cell analyzing table was generated in the past with an identical field being set as a target).

Here, in the following description, for the sake of simplification, a cell analyzing table that is newly generated this time is referred to as a "newly generated table." A cell analyzing table that was generated in the past on the same target as the newly generated table, that is, the past cell analyzing table in which the cell was observed at an observing time point different from that of the newly generated table, is referred to as an "already registered table." When a plurality of already registered tables is stored in the storage portion 44, the most recent table is selected as a target to be processed.

If the already registered table is stored in the storage portion 44 (yes), the process proceeds to step S207. On the other hand, if the already registered table is not stored in the storage portion 44, that is, if the table is generated for the first time (no), the CPU 43 completes the subroutine, and returns to the process in step S106.

In step S207, the CPU 43 uses the cell shape data of the already registered table and the newly generated table to perform an identity determination for determining the relationship between the cells of the tables.

The CPU 43 first reads the position data and the shape data from the already registered table.

Then, based on the position of the cell in the already registered table, the CPU 43 narrows down the range of matching performed on the cell in the newly generated table. Specifically, the CPU 43 excludes, from the target of the matching, a combination of cells whose positions on the images are significantly different between the tables. In particular, when the target cell is an adherent cell, the CPU 43 places importance on the position of the cell, and narrows the range as compared with when the target cell is a suspension cell.

Figure 6A:
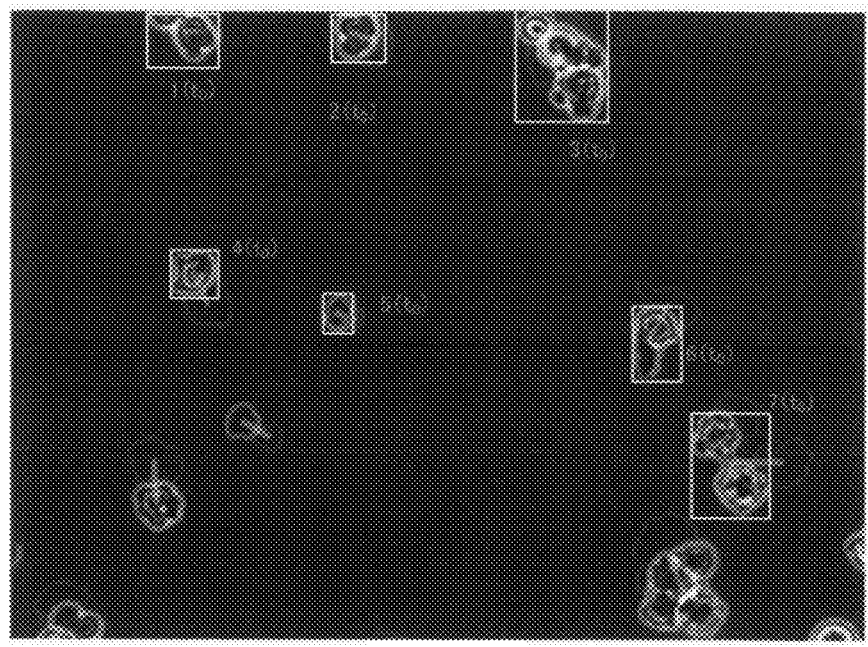
FIG. 6A is a diagram showing an example of a phase-contrast image at an observing time point $t_0$.
Figure 6B:
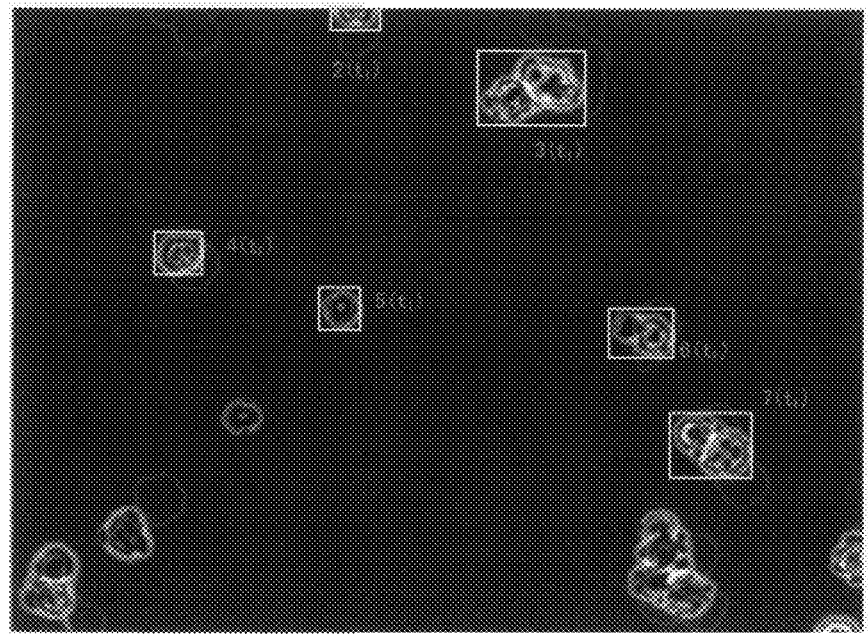
FIG. 6B is a diagram showing an example of the phase-contrast image at an observing time point $t_1$.

Then, the CPU 43 performs pattern matching on the outline shape of each cell in the already registered table and the newly generated table. Consequently, the CPU 43 estimates that a combination of cells having the highest similarity in the shape of the cell between the already registered table and the newly generated table is the identical cell. In FIG. 6, examples of the phase-contrast image at observing time points $t_0$ and $t_1$ are shown.

In step S208, the CPU 43 performs group determination for detecting the division or the attachment of the cell based on variations in the shape of the cell.

The CPU 43 first reads the already registered table and the newly generated table.

When, in the newly generated table, two or more single cells are newly generated in the vicinity of the position where an attached cell is present in the already registered table, the CPU 43 estimates that the attached cell present in the already registered table is divided in the newly generated table. Here, the CPU 43 records additional data indicating the identification code given to the cell dividing from the attached cell in the attribution data of the liked cell in the already registered table. In this way, the data of the cells before and after the division is made to correspond to each other, and is grouped.

When, in the newly generated table, a colony of cells is newly generated in the vicinity of the position where a plurality of cells is present in the already registered table, the CPU 43 estimates that the adjacent cells present in the already registered table are attached in the newly generated table. Here, the CPU 43 records additional data indicating the identification code given to the attached cell in the attribution data of the liked cell in the newly generated table. In this way, the data of the cells before and after the attachment is made to correspond to each other, and is grouped.

When a search is performed, the identification code of the additional data is referenced, and thus the CPU 43 can search culture information in the cell analyzing table on cells such as the divided cell from the cell of interest. Hence, the generation of the additional data improves convenience in serving as a data base.

In step S209, the CPU 43 achieves, based on the results of the identity determination (S207) and the group determination (S208), commonality of the identification codes given to the identical cell between the already registered table and the newly generated table. Thus, a plurality of cell analyzing tables stored in the storage portion 44 functions as the data base in which information of the identical cell is linked with the common identification code. Hence, any of the identification codes is used as a key, and various types of data are extracted from a plurality of cell analyzing tables at different observing time points, and thus it is possible to acquire observation data on the cell of interest which is continuous in the direction of the time axis.

In step S210, the CPU 43 compares the positions of the cells between the already registered table and the newly generated table to determine the movement amount of each cell. Furthermore, the CPU 43 divides the movement amount of the cell by the interval of shooting in the time lapse observation, and thereby also determines the movement speed of the cell. Then, the CPU 43 records the data of the movement amount and the movement speed of the cell in the storage portion 44 such that they correspond to the newly generated table.

After the completion of step S210, the CPU 43 completes the process of the subroutine, and returns to the process in step S106. Here, the description of the flowchart of FIG. 5 is completed.

(Description of the Search Process on the Culture Information)

An example of the search process that is performed on the culture information with the culture device 11 of the present embodiment will now be described with reference to a flowchart of FIG. 7. The example of FIG. 7 will be described on the assumption that the cell analyzing table is previously stored as the data base in the storage portion 44.

Figure 7:
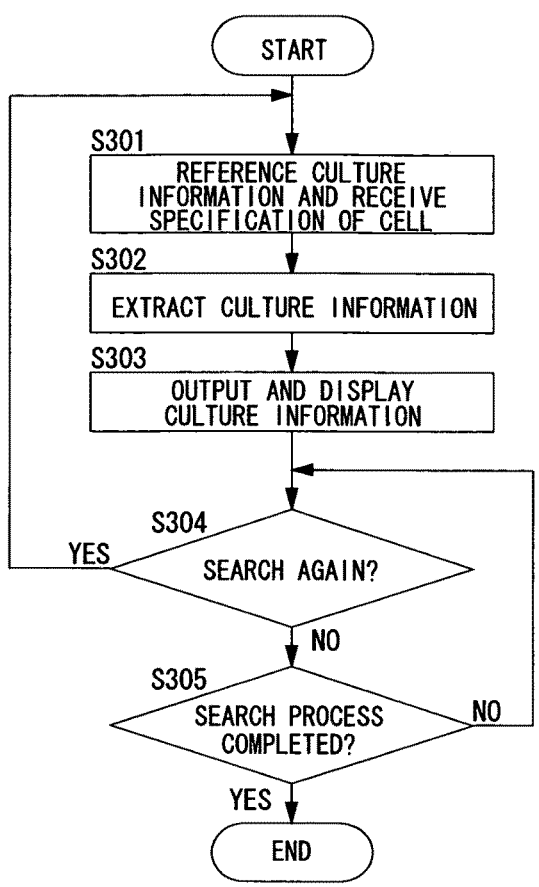
FIG. 7 is a flowchart showing an example of a search process on culture information in the present embodiment.

Here, the search process on the culture information shown in FIG. 7 is performed with the control device 41 of the culture device 11. The user performs various types of operations on the control device 41 through the terminal device 46 connected to the control device 41.

In step S301, the CPU 43 of the control device 41 starts up a sequence program of the search process according to the operation of the user through the terminal device 46.

Figure 8:
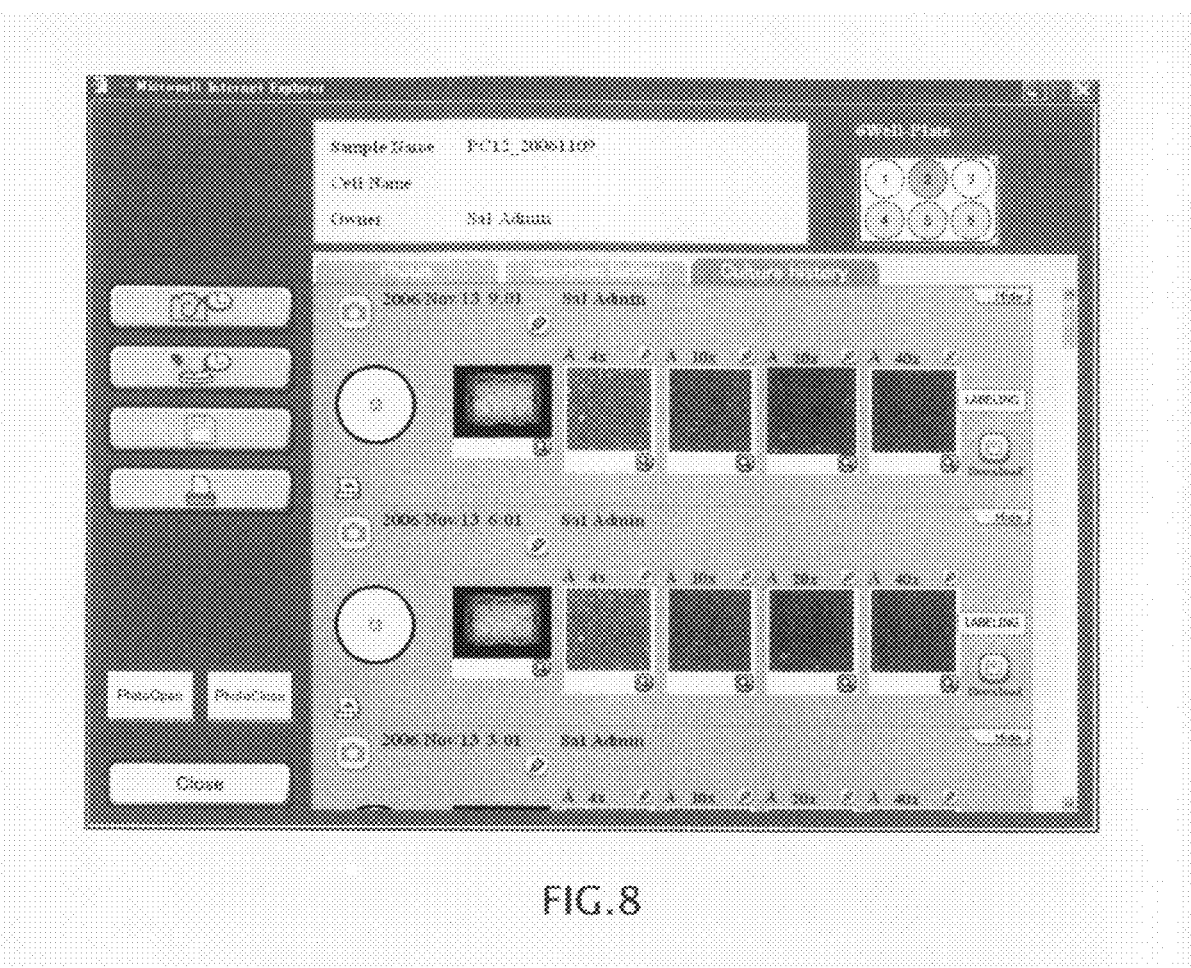
FIG. 8 is a diagram showing an example of a culture history screen.

As an example, a case where the search process is performed by the user through a culture history screen will be described. FIG. 8 is a diagram showing a state where the culture history screen is displayed on the monitor of the terminal device 46. In the culture history screen, the observation dates and times of a specific culture container 19 are displayed as a list. In this culture history screen, the overall observation image captured on the same observation date and time, four phase-contrast images (four times, ten times, twenty times, and forty times of magnification) and icons showing the image captured point within the culture container are displayed such that they correspond to the observation date and time.

Figure 9:
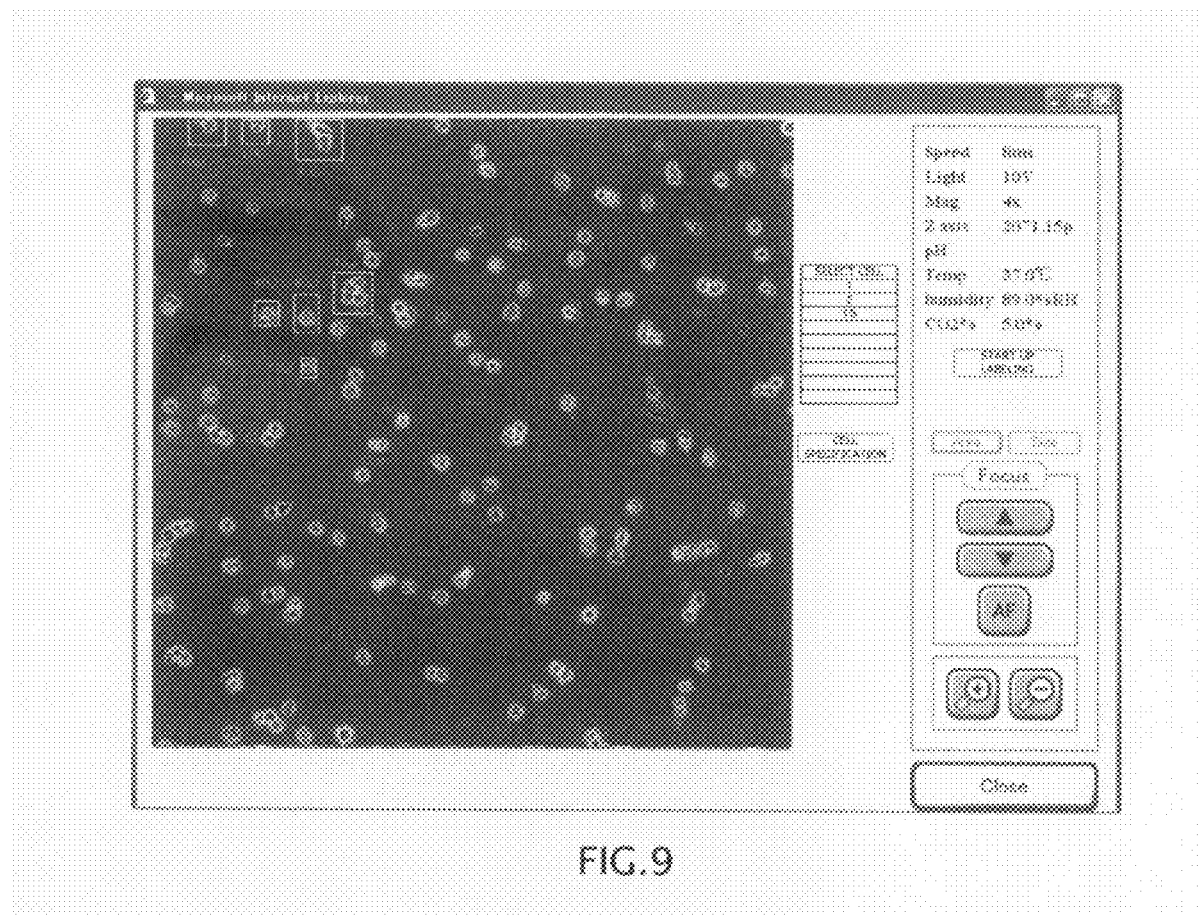
FIG. 9 is a diagram showing an example of the phase-contrast image where an identification code and a rectangular frame are superimposed on each other.

When the user clicks a "labeling" button in a GUI format in a state where any of the phase-contrast images is specified, the control device 41 outputs to the terminal device 46 the data of the phase-contrast image in which the identification code and the rectangular frame surrounding the cell are superimposed on each other. Then, the phase-contrast image in which the identification code and the rectangular frame are superimposed on each other is displayed on the monitor of the terminal device 46 (see FIG. 9).

Then, the user specifies, through the terminal device 46, the cell whose culture information is referenced. Specifically, the identification code on the phase-contrast image or the display of the rectangular frame is specified directly by the user with a pointer of the terminal device 46 and the like, and thus the identification code is input from the terminal device 46 to the control device 41.

In the present embodiment, the user can individually specify and input, from the phase-contrast image, the cell whose culture information is referenced, and thus it is possible to improve the operability at the time of the search process. In step S301, the user can specify a plurality of cells simultaneously with the terminal device 46.

In step S302, the CPU 43 uses the input identification code (S301) as the key to extract the culture information of the cell specified by the user from a plurality of cell analyzing tables stored in the storage portion 44.

In step S303, the CPU 43 outputs to the terminal device 46 the culture information of the cell extracted from a plurality of cell analyzing tables at different observing time points. Thus, it is possible to acquire, from the monitor of the terminal device 46, the culture information on the cell which is continuous in the direction of the time axis.

Here, according to the selection of the user, the CPU 43 can display, on the monitor of the terminal device 46, the culture information of the cell in any of the following display formats (1) to (3).

(1) The CPU 43 displays, on the monitor of the terminal device 46, the cell shape data, the fluorescence data and the attribution data at each observing time point in a format that can display them as a list for each of the identification codes.

Figure 10:
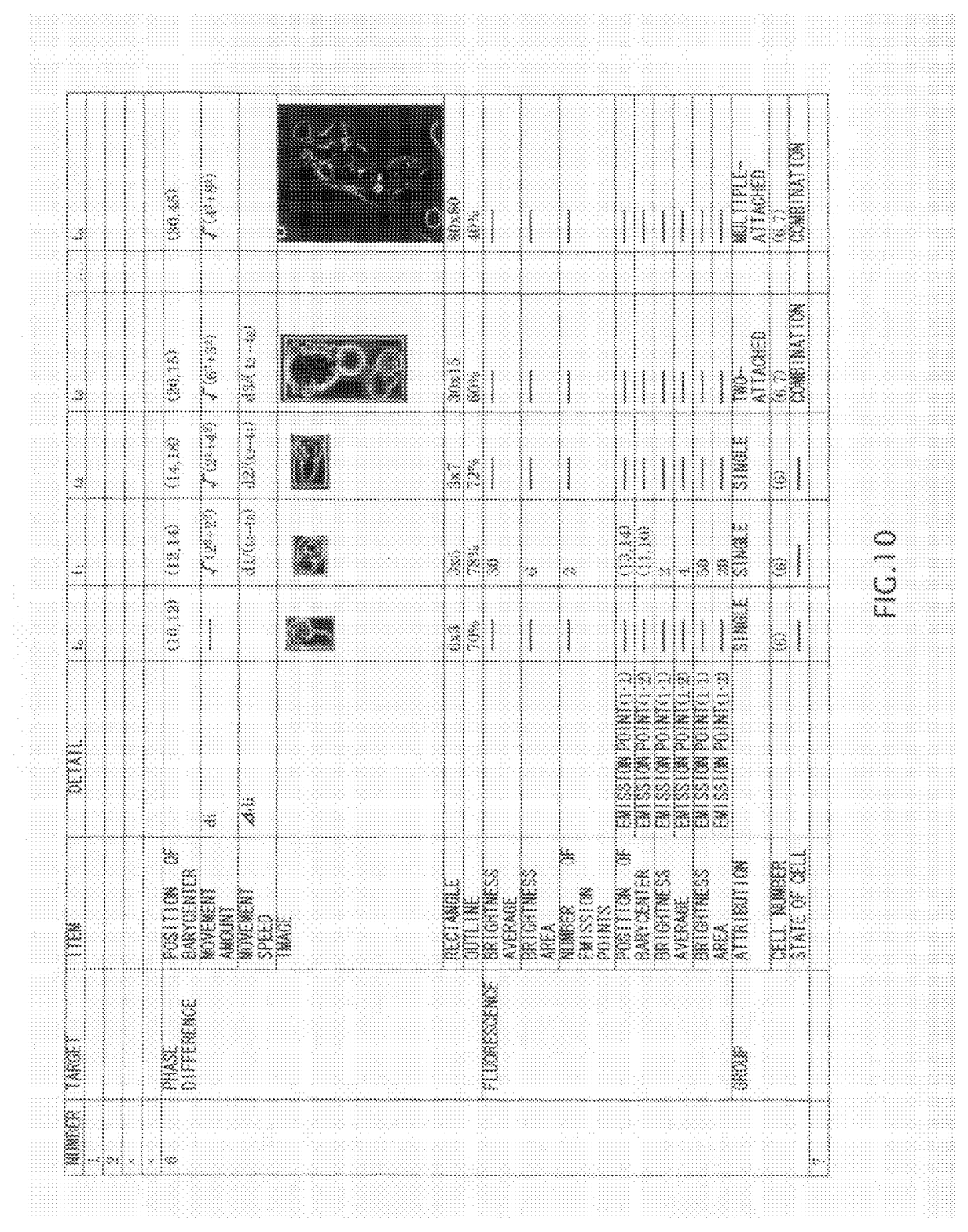

In FIG. 10, an example of a display screen listing the cell shape data and the like at each observing time point is shown. In this display screen, the information of the cell shape data, the fluorescence data and the attribution data at observing time points $t_0$ and $t_n$ is displayed.

Specifically, as items related to the cell shape data, "the position of the barycenter of the cell", "the movement amount and the movement speed of the cell", "the size of the rectangular frame" and "the ratio of the areas of the cells within the rectangular frame" are displayed in the format of a table on the monitor. The trimming image of the cell at each observing time point is also displayed on the screen.

As items related to the fluorescence data, "the number of fluorescence regions within the cell (the number of light emission points)" and "the brightness average value of fluorescence and the brightness area within the cell" are displayed in the format of a table on the monitor. In the screen, "the position of the barycenter of the fluorescence region", "the brightness average" and "the brightness area" are displayed for each of the light emission points on the monitor. When data indicating that there is no fluorescence region in the cell at a predetermined observing time point is recorded, "-" is displayed in the table of FIG. 10.

As items of the attribution data, "the attribution of the cell (such as a single cell or an attached cell)", "the identification code (cell number) recorded as the additional data" and "the state of the cell" are displayed in the format of a table on the monitor.

With the list display screen of FIG. 10, it is possible for the user to focus on a specific cell and grasp the variation of the state of the cell with time. For example, the user can obtain information such as variations in the cell shape and whether or not the cell division or the like occurs between the observing time points $t_0$ and $t_n$, and also whether or not to detect fluorescence and the intensity of the fluorescence between the observing time points $t_0$ and $t_n$.

Hence, the user grasps the behavior of a specific cell such as cell division, cell aging and cell death, and can obtain the fluorescence information of the cell. Moreover, the user analyzes the information of a specific cell that is continuous in the direction of the time axis, and thereby can evaluate the fluorescence information during the cell cycle.

(2) The CPU 43 displays, on the monitor of the terminal device 46, a screen that simultaneously shows both a tree diagram showing the kinetics of cell division using any of the cells as a base point and the time when each of the divided cells emits light.

Figure 11:
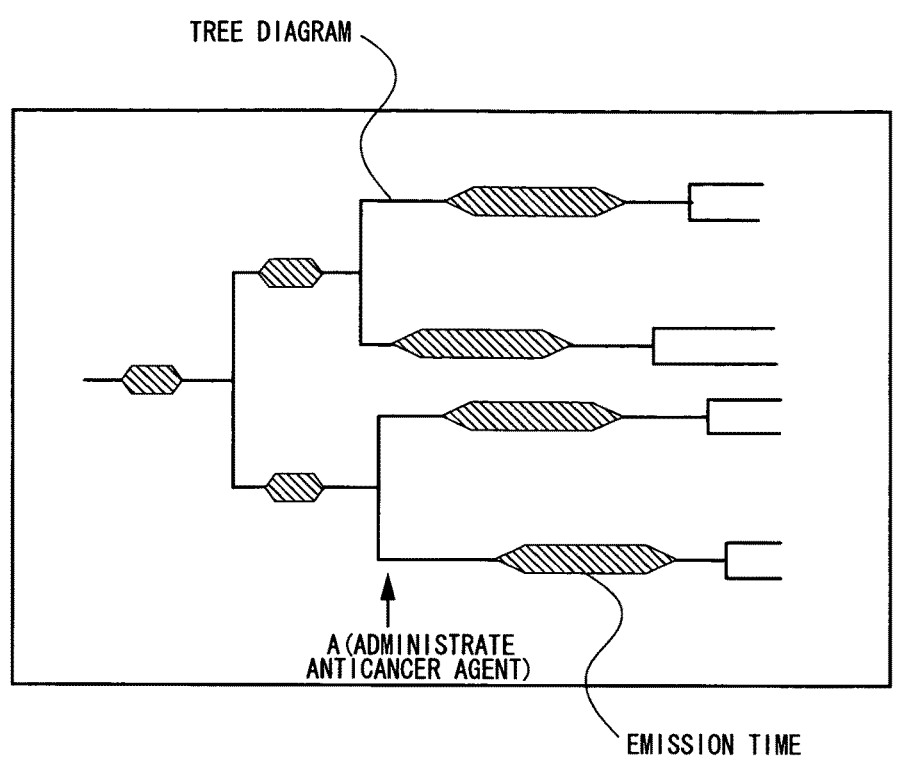
FIG. 11 is a diagram showing an example of a screen that displays an emission time of cells along with a tree diagram.

In FIG. 11, an example of the screen showing the tree diagram and the time when the cell emits light. In the example of FIG. 11, the horizontal axis represents the time. FIG. 11 shows the example where an ancestral cell fixes to the culture container 19, and thereafter the cell has divided three times.

When the screen of FIG. 11 is displayed, the CPU 43 references the additional data included in the data group extracted in step S302, and generates the tree diagram of the cell division including the cell of the specified identification code. Then, the CPU 43 references the fluorescence data of each of the divided cells included in the tree diagram, and determines the light emission time of each cell. Thereafter, the CPU 43 displays, on the monitor of the terminal device 46, a screen where the light emission time of each cell is superimposed and displayed on the tree diagram.

The display form of FIG. 11 visualizes the correlation between the cell cycle and the light emission time, and this makes it easy to, for example, observe the expression of a gene within the cell and determine the effects(s) of the tested drug(s) at the screening of medicines. For example, FIG. 11 shows a case where cancer cells treated to emit fluorescence only in the DNA replication time (synthesis phase) of the cell cycle are cultured, and where an anticancer agent is administrated at a predetermined time point A. In general, the duration of the cell synthesis phase is specific for the type of cell.

However, in the case of FIG. 11, after the time point A when the anticancer agent is administrated, the time (the duration of the synthesis phase) during which the cell emits fluorescence changes. Although there are various reasons why the cell cycle delays, it can be estimated that, in the example of FIG. 11, the anticancer agent administrated functions in the synthesis phase of the cell to inhibit the DNA replication.

(3) The CPU 43 may display, on the monitor of the terminal device 46, a screen showing results obtained by statistically processing the light emission times of a plurality of cells. For example, the CPU 43 displays, on the monitor of the terminal device 46, a histogram showing the correlation between the length of the light emission time and the number of cells, a graph showing the degree of displacement between the general cell cycle of the cell to be observed and the light emission time of each of the cells that have been observed or the like. In particular, when a significant number of cells are observed, the above-described display allows the tendency of cultured cells to be roughly grasped, and thus it is possible to improve the convenience of the device (the display screen in the case of (3) in step S303 is not illustrated.)

In step S304, the CPU 43 determines whether or not to receive, from the user, an input of an instruction to perform a search again. If the input is received (yes), the CPU 43 returns to step S301 and repeats the operation described above. On the other hand, if the input is not received (no), the CPU 43 transfers to step S305.

In step S305, the CPU 43 determines whether or not to receive an operation for the completion of the search process. If the input is received (yes), the CPU 43 completes the sequence program of the search process and transfers to a standby state. On the other hand, if the input is not received (no), the CPU 43 returns to step S304, and repeats the operation described above. Here, the description of the flowchart of FIG. 7 is completed.

The control device 41 of the culture device 11 of the present embodiment uses the phase-contrast image and the fluorescence image obtained by continuously imaging an identical field, and thereby generates the cell analyzing tables. Then, the control device 41 makes the cells correspond to each other between the tables based on the position and the shape of the cells between the cell analyzing tables, and focuses on the cells having commonality to allow a plurality of cell analyzing tables at different observing time points to be searched in the direction of the time axis.

Thus, it is possible for the user to track a specific cell and acquire information on the culture state of the cell that is continuous in the direction of the time axis, and it is also possible to obtain effective means for clarifying the relation between the shape and state of the cell and the cell cycle.

(Supplementary Notes on the Embodiment)

(1) The embodiment described above deals with the example where the control device 41 of the culture device 11 performs the program to store the cell analyzing tables as a database. However, in the embodiment described above, the terminal device 46 may perform a program including the image input process, a transparent observing image analyzing process, the fluorescence image analyzing process, the emitting determination process, the table generating process, the identity determination process and the database generating process.

(2) The embodiment described above deals with the example where the time lapse observation is performed on the fixed point of the culture container and thus the phase-contrast image and the fluorescence image of the identical field are captured on the cell. However, in the embodiment described above, the field of the imaging device 33*a* is moved according to the movement of the cell of interest to track the cell, and thus the phase-contrast image and the fluorescence image of the cell of the identical field may be captured.

(3) In the embodiment described above, instead of the phase-contrast image, the observation unit 22 may capture an image obtained by differential interference observation. The processes of the flowcharts in the embodiment described above are only an example, and the processes may be modified as necessary. For example, the order in which the fluorescence image and the phase-contrast image are captured may be changed. Moreover the process of generating the cell analyzing table in step S105 may be modified such that the control device 41 performs a batch process.

The many features and advantages of the embodiment are apparent from the detailed specification and, thus, it is intended by the appended claims to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. A non-transitory computer readable program recording medium storing a program causing a computer, which analyzes a culture state of cells by using a culture device including a temperature-controlled room culturing the cells under a predetermined environment condition and an imaging device capturing a microscope observing image of the cells in the temperature-controlled room, to execute:

generating a plurality of cell analyzing tables, each table corresponding to a different time at which the cells are observed, and each table generated through a process comprising reading data of a transparent observing image and data of a fluorescence image generated through continuous imaging of a same field by the imaging device, the images representing the cells at a certain observing time which differs among observation times respectively represented in the plurality of cell analyzing tables, generating identification data corresponding to each of the cells and cell shape data indicating a position and a shape of each of the cells by using the data of the transparent observing image, generating fluorescence data indicating a fluorescence detecting state within the field by using the data of the fluorescence image, and generating a cell analyzing table indicating a state of each of the cells and including the identification data, the identification data corresponded to both the cell shape data and the data of the fluorescence image;

matching a cell's identity across the plurality of cell analyzing tables for the different observing times by using the cell shape data, to thereby determine a correspondence relationship of the identification data between the plurality of cell analyzing tables for the different observing times; and generating, based on the correspondence relationship of the identification data, a database searchable in a time axis direction in which information of an identical cell is linked with common identification data among the plurality of cell analyzing tables for the different observing times.

2. The program recording medium according to claim 1, wherein the program causes the computer to further execute:
an emitting determination process determining an emission state of each of the cells by mapping the position of the cell indicated by the cell shape data used for one of the plurality of cell analyzing tables and a position of emission indicated by the fluorescence data used for the one of the plurality of cell analyzing tables.

3. The program recording medium according to claim 1, wherein
the computer further records the data of the transparent observing image used for one of the plurality of cell analyzing tables in the storage medium, and
the program causes the computer to further execute:
an image displaying process outputting the recorded transparent observing image to a display device;
a specifying process receiving specification of a cell to be searched among the cells included in the recorded transparent observing image; and
a result displaying process outputting an item of the one of the plurality of cell analyzing tables corresponding to the cell to be searched to the display device.

4. The program recording medium according to claim 1, wherein the program causes the computer to further execute:
a group determination process detecting a division or an attachment of the cells based on the shape of the cells; and
an additional data generating process generating additional data mutually associating the identification data of one of the cell analyzing tables corresponding to the cells being divided or attached when detecting the division or the attachment of the cells.

5. The program recording medium according to claim 1, wherein the program causes the computer to further execute:
a specifying process receiving specification of a cell to be searched; and
a result displaying process extracting data of the emission state relating to the cell to be searched among each of the plurality of cell analyzing tables and outputting a screen showing an emission time of the cell to be searched in the time lapse observation to a display device.

6. The program recording medium according to claim 5, wherein
the computer further records additional data mutually associating with the identification data corresponding to the cells being divided in the storage medium, and
in the result displaying process, outputs a screen that simultaneously indicates a tree diagram showing division-kinetics of the cells including the cell to be searched and the emission time of each of the cells being divided to the display device based on the additional data.

7. The program recording medium according to claim 5, wherein
in the result displaying process, a result obtained by statistically processing data of the emission time on the plurality of cells is output to the display device.

8. A culture state analyzing method using a computer which acquires data from a culture device including a temperature-controlled room culturing cells under a predetermined environment condition and an imaging device capturing a microscope observing image of the cells in the temperature-controlled room, the culture state analyzing method comprising:
generating a plurality of cell analyzing tables, each table corresponding to a different time at which the cells are observed, and each table generated through a process, executed by the computer, comprising
reading data of a transparent observing image and data of a fluorescence image generated through continuous imaging of a same field by the imaging device,
generating identification data corresponding to each of the cells and cell shape data indicating a position and a shape of each of the cells by uses the data of the transparent observing image,
generating fluorescence data indicating a fluorescence detecting state within the field by using the data of the fluorescence image, and
generating a cell analyzing table indicating a state of each of the cells and including the identification data, the identification data corresponded to both the cell shape data and the data of the fluorescence image;
using the computer to match a cell's identity across the plurality of cell analyzing tables for the different observing times by using the cell shape data and determine a correspondence relationship of the identification data between a plurality of cell analyzing tables for the different observing times; and
using the computer to generate, based on the correspondence relationship of the identification data, a database searchable in a time axis direction in which information of an identical cell is linked with common identification data among the plurality of cell analyzing tables for the different observing times.

9. The culture state analyzing method of claim 8, further comprising:
an emitting determination process in which the computer determines an emission state of each of the cells by mapping the position of the cell indicated by the cell shape data used for one of the plurality of cell analyzing tables and a position of emission indicated by the fluorescence data used for the one of the plurality of cell analyzing tables.

10. The culture state analyzing method of claim 8, further comprising:
a specifying process receiving specification of a cell to be searched by the computer; and
a result displaying process in which the computer extracts data of the emission state relating to the cell to be searched among each of the plurality of cell analyzing tables and outputs a screen showing an emission time of the cell to be searched in the time lapse observation to a display device.

* * * * *